United States Patent
Kuth et al.

(10) Patent No.: US 8,160,674 B2
(45) Date of Patent: Apr. 17, 2012

(54) UPPER BODY MRI SCANNER AND ASSOCIATED CONTROL METHOD

(75) Inventors: Rainer Kuth, Höchstadt (DE); Sebastian Schmidt, Weisendorf (DE)

(73) Assignee: Siemens Aktiengesellschaft, Munich (DE)

( * ) Notice: Subject to any disclaimer, the term of this patent is extended or adjusted under 35 U.S.C. 154(b) by 864 days.

(21) Appl. No.: 12/228,648

(22) Filed: Aug. 14, 2008

(65) Prior Publication Data
US 2009/0048505 A1 Feb. 19, 2009

(30) Foreign Application Priority Data
Aug. 14, 2007 (DE) .......................... 10 2007 038 382

(51) Int. Cl.
*A61B 5/00* (2006.01)
(52) U.S. Cl. ........ 600/415; 600/410; 600/411; 324/309; 324/318
(58) Field of Classification Search .................. 600/407, 600/410, 411, 413, 415, 418, 420; 382/128, 382/130, 131; 324/307, 309
See application file for complete search history.

(56) References Cited

U.S. PATENT DOCUMENTS

| | | | |
|---|---|---|---|
| 6,411,088 B1 | 6/2002 | Kuth | |
| 6,828,792 B1 | 12/2004 | Danby et al. | |
| 7,020,316 B2 | 3/2006 | Wei | |
| 7,072,497 B2 | 7/2006 | Faber et al. | |
| 7,680,525 B1 * | 3/2010 | Damadian et al. | 600/415 |
| 7,697,971 B1 * | 4/2010 | Green et al. | 600/415 |
| 7,734,078 B2 * | 6/2010 | Prince et al. | 382/130 |
| 2003/0068074 A1 | 4/2003 | Hahn | |
| 2003/0095696 A1 | 5/2003 | Chan et al. | |
| 2006/0173278 A1 * | 8/2006 | Wahl et al. | 600/410 |
| 2007/0110669 A1 * | 5/2007 | Driehuys et al. | 424/9.3 |
| 2008/0205717 A1 * | 8/2008 | Reeves et al. | 382/128 |

FOREIGN PATENT DOCUMENTS

| | | |
|---|---|---|
| CN | 1676096 A | 10/2005 |
| DE | 20009909 U1 | 9/2000 |
| DE | 100 07 598 A1 | 10/2000 |
| DE | 10105585 A1 | 7/2003 |
| DE | 102004015858 A1 | 10/2005 |

OTHER PUBLICATIONS

Office action from Chinese Patent Office with English Translation, Sep. 14, 2011, pp. 1-11.

\* cited by examiner

*Primary Examiner* — Brian Casler
*Assistant Examiner* — Amanda Lauritzen

(57) ABSTRACT

The invention relates to an upper body MRI scanner comprising a magnet arrangement for producing a horizontally oriented homogeneous main magnetic field, said magnet arrangement being designed to examine the upper body of a standing patient. An image acquisition unit is provided for continuously creating upper body image of the standing patient. A quality checking unit is designed for automatically determining a quality metric characterizing the quality of the upper body images. An imaging controller connected to the image acquisition unit and the quality checking unit is provided for activating the image acquisition unit and outputting signals for influencing the position and/or behavior of the patient as a function of the characteristic quality metric. An output unit connected to the image acquisition unit is used for displaying and/or storing at least some of the upper body images.

20 Claims, 3 Drawing Sheets

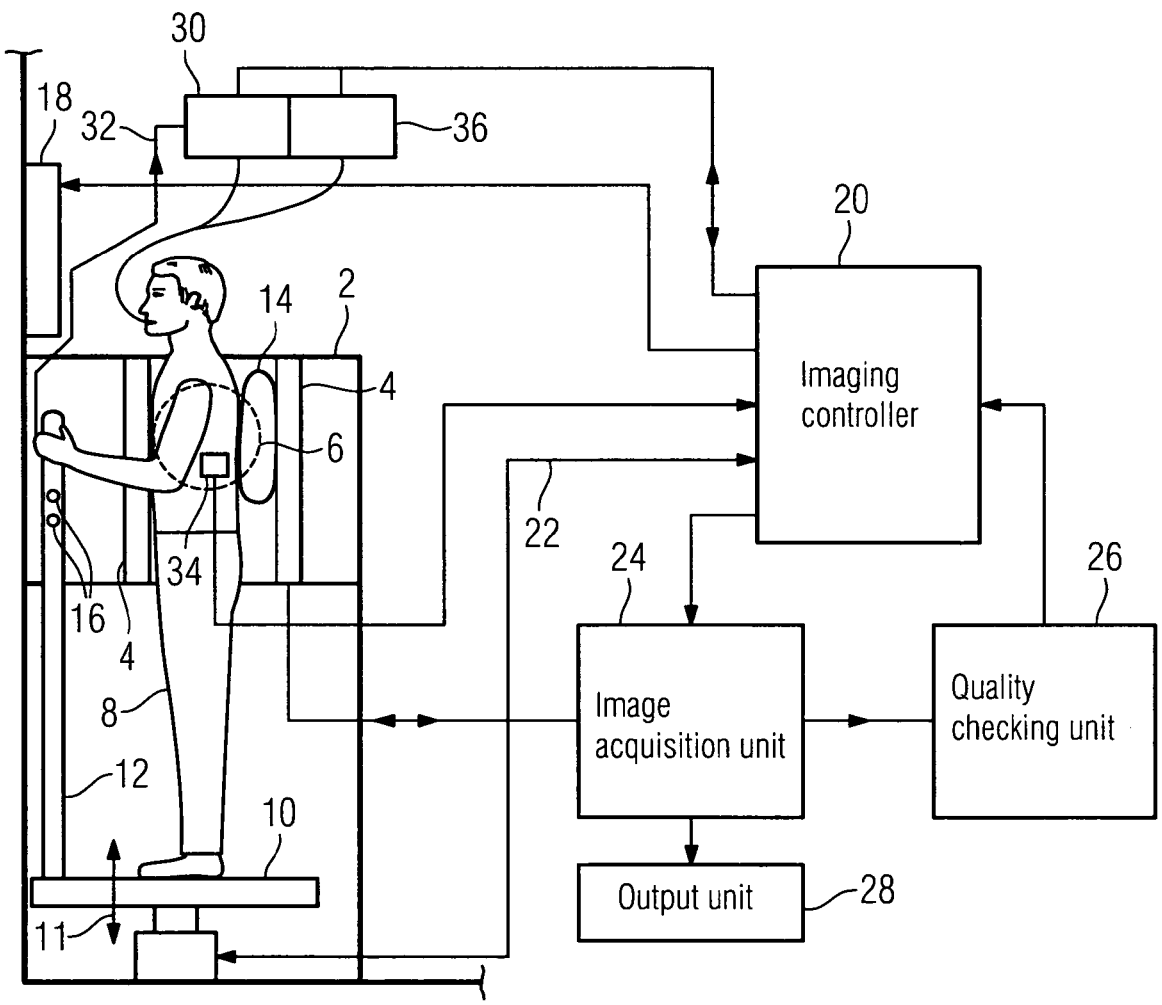

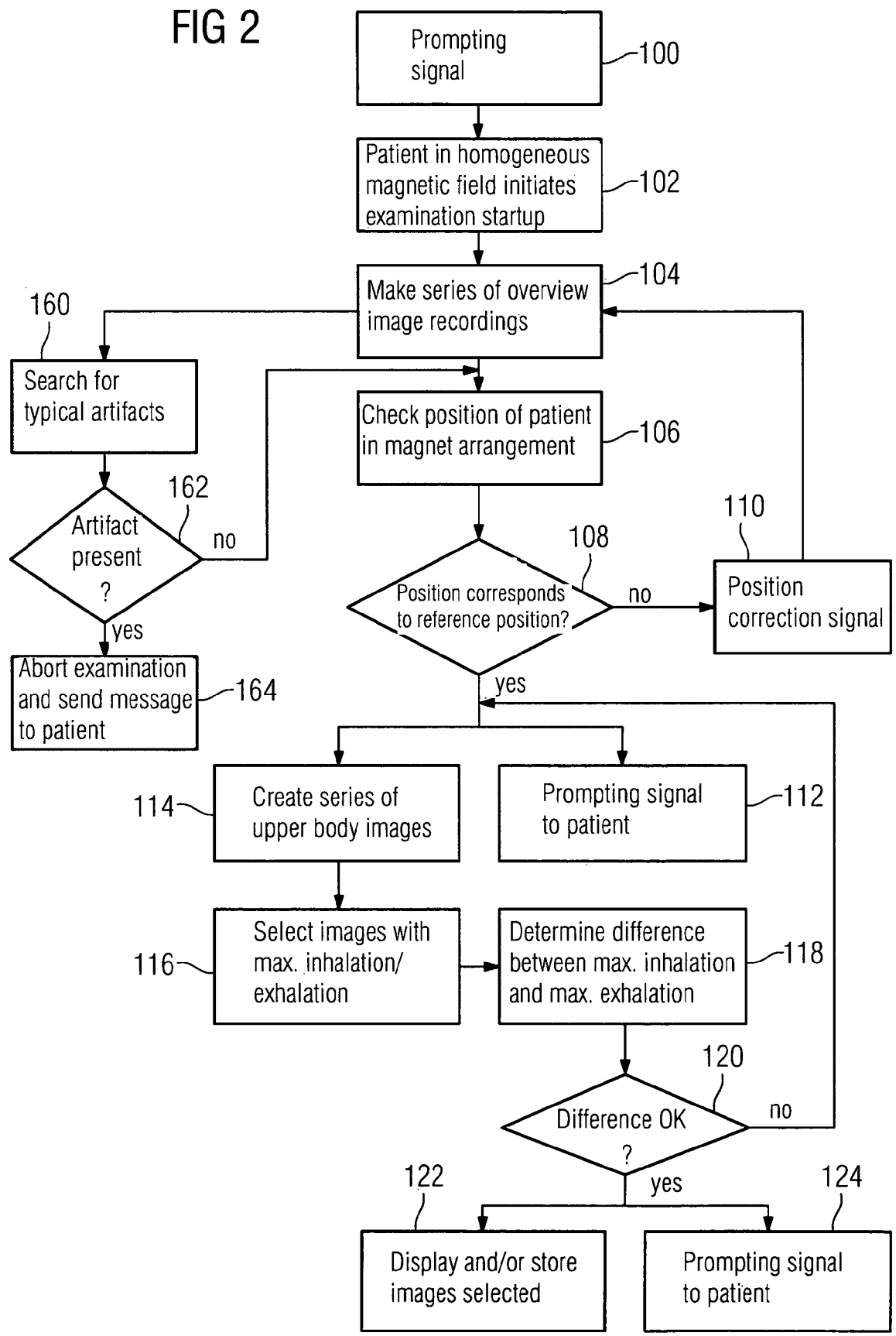

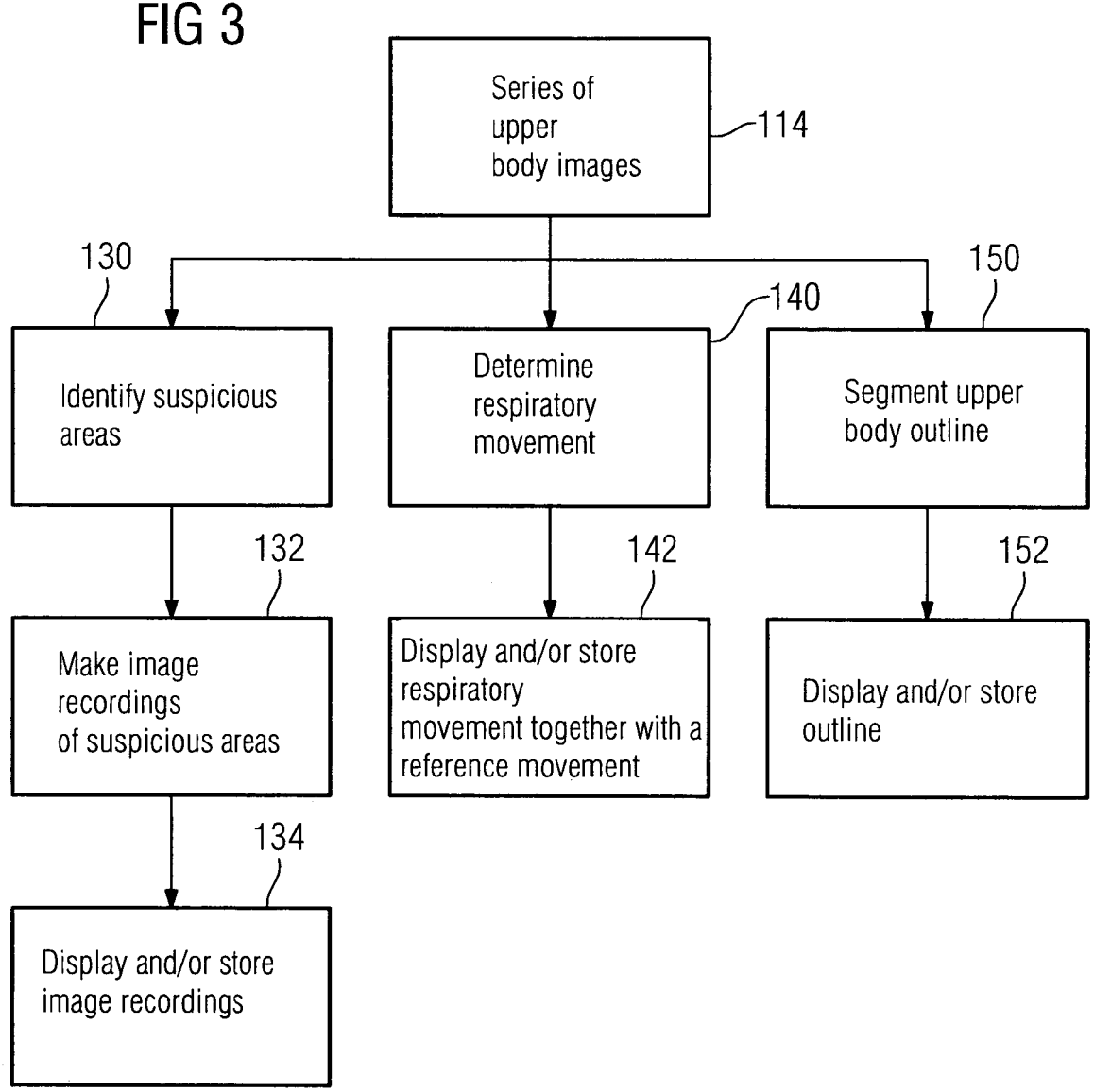

UPPER BODY MRI SCANNER AND ASSOCIATED CONTROL METHOD

CROSS REFERENCE TO RELATED APPLICATIONS

This application claims priority of German application No. 10 2007 038 382.9 filed Aug. 14, 2007, which is incorporated by reference herein in its entirety.

FIELD OF THE INVENTION

The invention relate to an upper body MRI scanner for examining the upper body of a standing patient. The invention likewise relates to a control method for an upper body MRI scanner of this kind.

BACKGROUND OF THE INVENTION

Diagnosing diseases of the cardiopulmonary system is one of the most frequently posed problems in medicine. For example, prior to an operation under anesthetic, investigations must be carried out to determine the patient's cardiopulmonary status. This is done in most cases on the basis of X-ray images. Consequently, the chest X-ray is the most frequent radiological examination of all.

Chest X-ray examination can be used to answer a large number of medical questions with varying degrees of success. This examination is expected to produce findings concerning the patient's cardiac function, e.g. whether signs of congestion of the pulmonary vessels are visible. It is also expected to provide indications of malignant diseases, such as so-called circular foci. Chest X-ray examination can also be used to detect infectious lung diseases such as pneumonia. Findings in respect of obstructive and restrictive lung diseases and indications of effusions are also possible. Chest X-ray examination has the particularly advantage of being inexpensive.

However, the chest X-ray method also has a number of disadvantages, chief among them being the patient's radiation load. Also the diagnostic value is low for some questions. For example, signs of congestion are a very indirect and only subjectively evaluable parameter in the X-ray photograph. Even obstructive and restrictive diseases are only detected indirectly and subjectively by a reduction or increase in lung marking. Moreover, chest X-ray examination does not allow quantifiability of results. Lastly, chest X-ray photographs are only comparable to a limited extent, as the visual appearance depends e.g. on the exposure and also on the depth of inhalation. Because of the large range of features to be evaluated, the examiner must be very experienced with such photographic images in order to make any kind of reliable assessment. On the other hand, the radiologist has to evaluate a large number of images daily, the danger being that indications of diseases will be overlooked in one image or another.

A number of methods are now known which enable the abovementioned diseases to be better and more accurately detected than by chest X-ray. For example, heart diseases can be better and more accurately found using echo cardiography, i.e. an ultrasound examination of the heart. X-ray computed tomography likewise enables the condition of lung and heart to be imaged and also diagnosed with a high degree of accuracy. Finally, magnetic resonance imaging (MRI) permits excellent vascular analysis and soft tissue differentiation.

However, none these methods has been able to replace the chest X-ray. The main reason for this are the comparatively high costs of these alternative methods, which stand in the way of their being used routinely and therefore frequently. A significant portion of the examination costs comes from producing the images. For MRI, for example, particularly qualified personnel are required in order to carry out the examination so as to ensure high diagnostic quality. It is therefore desirable to make it attractive to use MRI also routinely as a more informative examination method than chest X-ray.

U.S. Pat. No. 6,411,088 (corresponding to DE 100 07 598 A1) discloses an MRI scanner for creating a radiological image. The scanner incorporates a C-shaped main field magnet system which is fixed to a wall of a room. To create a radiological image, a patient to be examined enters the side opening of the C-profile. The scanner is provided with handles so that, while the image is being taken, the patient is able to stand as still as possible by pulling or pressing against a surface designed for that purpose, thereby avoiding motion artifacts in the resulting image. The scanner also comprises a gradient coil system, an RF transceiver, a display and operator control device and a central control system which is appropriately connected to the gradient coil system, the RF transceiver and the display and operator control device. In particular, with the MRI scanner described there, refocused gradient echo sequences e.g. implemented as a true FISP sequence can be executed for the examination.

US patent application publication US 2003/0095696 A1 describes an apparatus and a method for computer-aided diagnosis of small pulmonary nodules. Two main steps are carried out for pulmonary nodule assessment. First the locations of possible nodules must be identified. This is followed in the next step by characterization to evaluate the possibility that a detected nodule contains cancer tissue. Characterization is based on the growth rate of the nodule, which requires comparing the sizes in two images taken at different times. A method of detection and feature extraction for size characterization is also described there.

US patent application publication US 2003/0068074 A1 describes a computer system and a method for segmentation for the purpose of imaging and quantifying the volume of the segmented region in digital images, wherein a watershed transformation of the digital image is performed. In post-processing, the picture elements which must be assigned to a least one catchment basin are implemented using grey value based segmentation, visualization by means of a transfer function or volume determination using histogram analysis.

A method for computer-aided detection of pulmonary nodules including these fed by vessels is known from U.S. Pat. No. 7,020,316 B2, wherein a seed point is automatically detected from a plurality of images. The seed point defines a volume of interest (VOI). Finally, the shape or outline of projections of the volume of interest is analyzed to detect nodules.

SUMMARY OF THE INVENTION

The object of the invention is now to specify an upper body MRI scanner with which upper body recordings of a patient can be inexpensively produced, so that even routine examinations of high diagnostic quality can be carried out inexpensively. A control method for an upper body MRI scanner of this kind will also be proposed.

The first object is achieved by the subject matter of the first independent claim, according to which the upper body MRI scanner comprises a magnet arrangement for generating a horizontally oriented homogeneous main magnetic field, said magnet arrangement being designed to examine the upper body of a standing patient, an image acquisition unit for continuously creating upper body images of the standing patient, a quality checking unit for automatically determining a quality metric characterizing the quality of the upper body images, an imaging controller connected to the image acquisition unit and the quality checking unit for activating the image acquisition unit and for outputting signals for influencing patient position and/or behavior as a function of the characteristic quality metric, and an output unit connected to the image acquisition unit for displaying and/or storing at least some of the upper body images.

The second object is achieved by the subject matter of the second independent claim, according to which the control method for the upper body MRI scanner according to the invention comprises the following control steps: the imaging controller gives a prompting signal to the patient to position himself in the upper body MRI scanner, the imaging controller initiates a series of overview image recordings as soon as the patient is in the homogeneous magnetic field of the magnet arrangement, the quality checking unit checks the position of the patient in the magnet arrangement on the basis of the overview image recordings, the imaging controller outputs a position correction signal if the patient's position does not correspond to a reference position, the imaging controller outputs a signal to create a series of upper body images of the patient and a prompting signal to the patient to inhale and exhale if the patient's position corresponds to the reference position, the imaging controller selects from the series a first image representing the state of maximum inhalation, and selects from the series a second image representing the state of maximum exhalation, and the output unit displays the first and second image and/or stores them.

The underlying idea of the invention is to completely automate MR imaging of the lung in order to reduce the costs mainly associated with the scanning process. The automation approach can be seen in the fact that the patient can independently assume his examination position in the MRI scanner in a simple manner. To this end it is proposed that the patient be examined standing up in the scanner. The scanner is additionally designed for continuous image acquisition and automatic evaluation of image quality. A successful examination is assisted by automatically influencing the patient's position or behavior. The position or behavior influencing signals are applied to a movable patient platform or more specifically to an information unit for the patient. By means of the information unit, appropriate behavior instructions for the patient are issued in a recognizable manner, e.g. via voice commands. Automatic patient position or behavior influencing during simultaneously ongoing image acquisition with automatic evaluation of image quality are carried out until sufficient image quality is achieved. This makes it possible to perform particularly inexpensive MRI lung scanning, because it obviates the need for both qualified personnel and a sophisticated control console for the scanner.

According to advantageous embodiments, the patient is prompted via a computer-generated voice to enter the magnet arrangement, hold on to two handles and place his/her chest on a surface intended to the purpose, the patient standing upright on a vertically movable platform. Handles are connected to the platform and move with it.

In an advantageous embodiment, the control method then provides for automatic imaging of the patient in real time. Appropriate magnetic resonance sequences are known. For imaging of this kind, for main magnetic field strengths up to 1 tesla, the sequence known as real time true FISP and thereabove the sequence known as HASTE and derivatives of these two types of sequence are particularly suitable.

In another advantageous embodiment, it is assessed in real time on the basis of the recordings obtained whether the patient's position is correct, i.e. corresponds to a reference position. For this purpose easily identifiable and characteristic features in the image dataset are identified and evaluated.

In an advantageous embodiment, it is interrogated whether the spinal column which is clearly visible and can be reliably detected using appropriate pattern recognition methods is located centrally in the image dataset. This likewise applies to the clearly visible and detectable lung whose complete imaging is being tested for. Appropriate methods for identifying the lung or bones in the image are known, e.g. from the publications US 2003/095696 A1 or US 2003/068074 A1 already cited in the introduction. If testing indicates that the patient's position does not correspond to the reference position, either the patient platform is moved vertically, or the patient is requested by voice commands to change position until the patient is standing in the correct position.

Another advantageous embodiment is characterized in that when the patient has been requested to inhale or exhale the lung density is measured or the lung is segmented and its volume determined. Corresponding methods are likewise known from US 2003/095696 A1 already cited in the introduction.

From the acquired datasets, those representing the state of maximum inhalation or maximum exhalation are selected. Anatomically, the state of maximum inhalation corresponds to minimum lung tissue density, i.e. maximum lung volume. The state of maximum exhalation is automatically detectable via the criterion of maximum lung tissue density or minimum volume. Both criteria are detectable in the magnetic resonance images obtained.

In other advantageous embodiment, respiration quality is checked. If the difference between maximum inhalation and maximum exhalation falls below a limit value, it is assumed that the patient has not breathed deeply enough. Scanning is repeated after appropriate instructions have been issued to the patient.

Similarly, according to another advantageous embodiment scanning is repeated if the images show signs of blurring. This evaluation is likewise carried out in an automated manner.

Finally the patient is informed that the examination is complete and he can leave the scanner independently.

In another advantageous embodiment, the patient is requested to breathe in and out as quickly as possible, the time between maximum inhalation and maximum exhalation being measured. From this test, the change in lung volume over time, i.e. the respiratory air flow, can be measured in order to diagnose obstructive lung diseases.

In another advantageous embodiment, computer aided detection methods are applied directly to the datasets during acquisition. Such methods are known from U.S. Pat. No. 7,020,316 B. If a suspicious area is identified, further image recordings of this area are immediately prepared, it being possible to change the slice thickness and other imaging parameters.

In another advantageous embodiment, the patient is fixed in a standing position inside the upper body MRI scanner by an inflatable cushion or by one or more displaceable propping devices. Advantageously, the patient can himself control the contact pressure by actuating an input device.

In another advantageous embodiment the patient can see on a display whether he has positioned himself centrally and, in concise form, which breathing commands are being issued. His respiratory movements are advantageously extracted from the magnetic resonance signal and likewise displayed in real time on the display unit.

In another advantageous embodiment, the outline of the patient's chest segmented from the MR image dataset is displayed together with an outline of the homogeneous region of the scanner.

In another advantageous embodiment, the patient's current respiratory phase is displayed in relation to a reference. The reference can be determined from the previous respiratory pattern or constitute an average pattern based on size, sex etc. of the patient.

In another advantageous embodiment an automatic position change of the patient platform is displayed on the patient display or also announced by voice output or warning signal.

Another advantageous embodiment is characterized in that the MR image data is searched for typical artifacts. Examples of such artifacts are belt buckles and bra wires. Generally when such typical artifacts are detected scanning is stopped and the patient is requested to remove the troublesome items of clothing.

Further advantageous embodiments of the invention are defined in the sub-claims and will emerge from the figures and associated description.

BRIEF DESCRIPTION OF THE DRAWINGS

An exemplary embodiment of the invention will now be explained with reference to the accompanying drawings in which:

FIG. 1 schematically illustrates the main functional units of an upper body MRI scanner, FIG. 2 is a flowchart showing the main steps of a control method for the upper body MRI FIG. 3 is a flowchart showing additional quality inspection steps for the MR images obtained using the upper body MRI scanner.

DETAILED DESCRIPTION OF THE INVENTION

The upper body MRI scanner shown in FIG. 1 with its main functional units comprises an open magnet arrangement 2 with two oppositely disposed poles 4 between which a homogeneous magnetic field is produced in an imaging volume 6. The magnet poles 4 are interconnected via a magnetic flux return path so as to produce an altogether C-shaped magnet arrangement 2. Possible magnetic field generators include preferably permanent magnet arrangements or even electrically normal-conducting solenoids. The magnetic field strength in the imaging volume is in the order of 0.35 teslas. The magnet arrangement 2 is open to the side so that a patient 8 to be examined can step onto a patient platform 10 supported on the base 6 below the imaging volume 6 in order to assume a standing examination position in the magnet arrangement 2. The patient platform comprises a lifting unit for positioning the patient 8 vertically. The lifting unit is symbolized by the double arrow 11. The upper body MRI scanner additionally comprises a gripping rod 12 which the patient 8 can hold on to during scanning. During scanning, the patient 8 places his chest on the left magnet pole 4 and grasps the laterally disposed gripping rods 12. An inflatable cushion 14 is also provided which additionally fixes the patient 8 inside the magnet arrangement 2 between the magnet poles 4. The contact pressure of the inflatable cushion 14 can be adjusted by the patient 8 himself via controls 16 disposed on the gripping rod 12. Disposed in the line of vision of the patient 8 above the magnet arrangement 2 is an information unit 18 for visual and audible messages and behavior instructions to the patient.

In addition to the functional units generally necessary for diagnostic MR equipment, such as RF and gradient system as well as a controller for sequence generation, the upper body MRI scanner incorporates a special imaging controller 20. The imaging controller 20 is connected to the patient platform 10 via a bidirectional signal line 22. The imaging controller 20 gives the information unit 18 information and instructions for the patient 8 to be examined concerning the start, progress and end of scanning. An image acquisition unit 24 now continuously produces MR images of the upper body of the patient 8 according to the control signals predetermined by the imaging controller 20.

The MR images produced by the image acquisition unit 24 are analyzed in a quality checking unit 26 for a plurality of different features. The features are compared with references in order to create a quality metric. As a function of the quality metric, the imaging controller 20 in turn generates corresponding signals for the examination sequence.

In addition, an output unit 28 is connected to the image acquisition unit 24. The output unit 28 comprises an image display unit and memories for storing the MR images produced.

A drug administering device 30 is likewise connected to the imaging controller 20 in order to control the creation of upper body images as a function of the administration of drugs. This is accompanied by marking of the upper body images obtained during drug administration with the comment "after administration of therapeutic agent". The patient can start and stop the administration of drugs himself. For this purpose the drug administering device 30 has corresponding controls symbolically illustrated in FIG. 1 by an operative connection 32. On commencement of drug administration, the upper body images are created using particular parameters, e.g. high frame rate, in order to achieve time- and locally resolved imaging of the effects of the therapeutic agent.

In addition, an ECG recording and triggering device 34 is also connected to the imaging controller 20, enabling the creation of upper body images to be controlled by the cardiac phase. To record the upper body images, standard methods of the type employed for cardiac imaging can be used.

Finally, the imaging controller 20 is also connected e.g. to a device for dispensing image enhancing gases 36, e.g. hyperpolarized gases. Hyperpolarized gases are added to the breathing air and can significantly improve the upper body images in the lung region. As hyperpolarized gases generally possess a different resonant frequency from that of protons, the scanner is accordingly designed for imaging with a plurality of operating frequencies which are switchable.

FIG. 2 shows a control method for the upper body MRI scanner according to FIG. 1 in the form of a block diagram. The examination begins with a prompting signal 100 to the patient 8 to step between the magnet poles 4, hold on to the two handles 12 and place his chest on one of the magnet poles 4. The prompting signal 100 is audibly given to the patient 8 by a computer-generated voice. As soon as the patient 8 is in the homogeneous magnetic field or in the imaging volume 6, which is ascertained e.g. by a pressure sensor disposed on the patient platform 10, a start signal is fed to the imaging controller 20 via the bidirectional line 22 in control step 102, in response to which MR recordings of the upper body are created by the image acquisition unit 24 in real time, e.g. using a real time true FISP sequence. Such sequences are well known and variously described elsewhere. The MR recordings are produced in a series as overview image recordings with reduced resolution for time reasons, the corresponding step being denoted by reference character 104.

In control method step 106, the quality checking unit 26 then continuously checks the position of the patient 8 in the magnet arrangement 2 in the individual overview image recordings. This likewise takes place in real time, easily identifiable features in the image dataset being identified, examined in terms of their position and then, in step 108, compared with a reference position. During position checking 106 and comparison 108 it is e.g. verified whether the spinal column of the patient 8 runs centrally in the image dataset or whether the lungs are completely imaged. Corresponding methods for lung or bone identification in the image are known to the average person skilled in the art and are described e.g. in US 2003/095696 A or US 2003/068074 A already cited in the introduction.

If the position of the patient 8 does not yet correspond to the reference position, e.g. if the spinal column is off-center or lungs are only partially imaged, the quality checking unit 26 sends an appropriate signal to the imaging controller 20, whereupon a position correction signal 110 is generated in the imaging controller 20. Depending on the ascertained mispositioning of the patient, either an appropriate lifting or lowering signal is fed to the adjusting device of the patient platform 10 or the patient is requested via the information unit 18 to change position, e.g. with the audible request "Please move slightly to the left". In parallel with this, in step 104, overview images are continuously taken and, in steps 106 and 108, the current position is determined and compared with the reference position.

If the position of the patient 8 is detected by the quality checking unit 26 as coinciding with the reference position, an appropriate signal is fed to the imaging controller 20, thereby starting the actual examination. The imaging controller 20 first sends a signal to the patient prompting him to begin deliberately inhaling and exhaling deeply (step 112). During the inhalation and exhalation of the patient 8, a series of upper body images is created (step 114). The resolution and quality of the upper body images are generally higher than in the overview image recordings, in any case high enough in order to be able to recognize the features necessary for diagnosis in the upper body images. From the upper body images now obtained, in step 116 upper body images with maximum inhalation and exhalation of the patient 8 are selected in the quality checking unit 26. For example, the state of maximum inhalation can be ascertained from the upper body images by evaluating the minimum density and/or maximum volume of the lung. The state of maximum exhalation is typically ascertained from the upper body images via the maximum density and/or minimum volume of the lung. In step 118, these selected upper body images with maximum inhalation and maximum exhalation are checked by determining the difference between the two upper body images. The difference is assessed in step 120. If the difference is less than a limit value, it is assumed that the patient 8 has not breathed deeply enough and the measuring process is repeated. The measuring process is likewise repeated if the upper body images show signs of blurring. If the difference between maximum inhalation and maximum exhalation has been found to be sufficient by the quality checking unit 26, the examination is terminated, the selected upper body images are displayed and/or stored in the output unit 28, as symbolized by step 122. In step 124, the patient 8 is also informed via the information unit 18 that the examination is complete and he can leave the upper body MRI scanner.

The quality checking unit 26 also evaluates the upper body images for controlling the administration of drugs. If on the basis of reducing proton density in consecutive upper body images the quality checking unit detects an incipient inhalation cycle, an appropriate signal is fed to the drug administering device 30 via the imaging controller 20 in order to initiate drug administration. A pneumatically or hydraulically operated valve in the drug administering device then opens a line from the drug dispenser to the patient.

Another quality test is likewise also shown in FIG. 2, wherein the quality checking unit 26 continuously checks whether the overview image recordings contain typical artifacts. Typical artifacts of this kind are produced by metal items in the patient's clothing, such as bra underwiring or belt buckles. Such typical artifacts are identified in step 160. As they produce strong and characteristic picture elements, they can be easily identified by pattern recognition methods. If an artifact is detected in the upper body images (step 162), the examination is aborted and an appropriate message is communicated to the patient 8 via the information unit 18.

FIG. 3 is a block diagram showing an overview of other checks carried out in the quality checking unit 26. The quality checking result is fed to the imaging controller 20 which then generates appropriate control signals for the upper body MRI scanner.

In step 130, another test is performed such that, from the series of upper body images 114, suspicious areas are directly identified using computer-aided detection methods during acquisition. In step 132, further image recordings of identified areas are then prepared by the image acquisition unit 24 after an appropriate signal from the imaging controller 20, the parameters for the image recordings being selected such that optimum and diagnostically useful images are produced, e.g. for the imaging a smaller slice thickness and therefore a better resolution in the slice direction is set than in the upper body images. In step 134, the image recordings of the suspicious areas are then displayed and/or stored in the output unit 28.

In step 140, another analysis carried out by the quality checking unit 26 determines the respiratory movement in the series of upper body images 114. The respiratory movement is displayed and/or stored in step 142. It can also be displayed together with a reference respiratory movement produced e.g. in relation to the previous respiratory movements or also displayed as an expected respiratory movement of the patient 8 on the basis of the size, sex, etc. of the patient 8.

Another analysis performed in the quality checking unit 26 consists of segmenting the outline of the upper body (step 150). In step 152, the outline of the upper body together with the outline of the homogeneous area in the diagnostic MRI scanner or of the imaging volume 6 is displayed to the patient 8 by means of the information unit 18, with simultaneous storing together with the images produced in this position of the patient by means of the output unit 28.

The invention claimed is:

1. An upper body MRI scanner for examining a patient, comprising:
    a magnet unit configured to produce a horizontally oriented homogeneous main magnetic field;
    an image acquisition unit configured to record an upper body image of the patient;
    a quality checking unit configured to automatically determine a quality metric characterizing a quality of the upper body image;
    an imaging controller connected to the image acquisition unit and the quality checking unit that is configured to activate the image acquisition unit and output a signal for correcting a position of the patient as a function of the characteristic quality metric;
    wherein the magnet unit is connected to a displacement mounted patient platform that is configured to change a position according to the signal, and
    wherein the patient platform comprises a lifting unit.

2. The upper body MRI scanner as claimed in claim 1, wherein the magnet unit is connected to a fixing device that fixes an upper body of the patient.

3. The upper body MRI scanner as claimed in claim 1,
wherein the image acquisition unit continuously records the upper body images in real time, and
wherein the quality checking unit automatically determines the quality metric in real time.

4. The upper body MRI scanner as claimed in claim 1, wherein the patient is in a standing position.

5. The upper body MRI scanner as claimed in claim 1, further comprising an output unit connected to the image acquisition unit that displays or stores the upper body image.

6. The upper body MRI scanner as claimed in claim 1, further comprising an information unit connected to the displaceably mounted patient platform and configured to change a position of the lifting unit in response to a correction signal.

7. A method for controlling an upper body MRI scanner for examining a patient, comprising:
delivering a prompting signal to the patient to position on a patient platform in the upper body MRI scanner;
recording a series of overview image recordings when the patient is in a homogeneous magnetic field of a magnet unit of the upper body MRI scanner;
checking a position of the patient in the magnet unit based on the overview image recordings;
outputting a position correction signal with an information unit if the position of the patient does not correspond to a reference position;
outputting a further prompting signal to the patient to inhale and exhale if the position of the patient does correspond to the reference position;
recording a series of upper body images of the patient; and
selecting a first image from the upper body images representing a maximum inhalation and a second image from the upper body images representing a maximum exhalation
changing a position of a displaceably mounted patient platform according to the correction signal from the information unit, and
wherein the patient platform comprises a lifting unit.

8. The method as claimed in claim 7,
wherein a difference between the first and the second images is automatically determined, and
wherein the examination is repeated if the difference exceeds a difference limit value.

9. The method as claimed in claim 7, wherein the position of the patient in the overview image recordings is determined based on an anatomical feature of the patient.

10. The method as claimed in claim 7, wherein a lung density value or a lung volume is determined from the upper body images for selecting the maximum inhalation and the maximum exhalation.

11. The method as claimed in claim 7, wherein a change in a lung volume over time is determined from the upper body images when the patient is requested to breathe as quickly as possible.

12. The method as claimed in claim 7, wherein a suspicious area of the patient is identified from the upper body images using a computer-aided detection method and a further image recording is recorded for the suspicious area.

13. The method as claimed in claim 7,
wherein an information signal for the patient is generated and outputted at a start of the examination, or during the examination, or at an end of the examination, and
wherein the information signal comprises a respiratory movement that is derived from the upper body images.

14. The method as claimed in claim 7, wherein a chest outline of the patient is segmented from the upper body images and displayed together with an outline of a region of the homogeneous magnetic field.

15. The method as claimed in claim 7, wherein a respiratory phase is determined from the upper body images and displayed together with a reference respiratory phase.

16. The method as claimed in claim 7,
wherein a typical artifact is searched for the overview image recordings or the upper body images, and
wherein the examination is aborted and the patient is issued with an instruction if the typical artifact is present.

17. The method as claimed in claim 7,
wherein an administration of drug is detected and controlled, and
wherein the upper body images recorded during the administration of drug are marked.

18. The method as claimed in claim 7, wherein the upper body images are recorded as a function of an electrophysiologal signal of the patient.

19. The method as claimed in claim 7, wherein an image enhancing gas is administered based on a control signal.

20. The method as claimed in claim 7, wherein the first and the second images are displayed or stored.

* * * * *